(12) United States Patent
Pochy et al.

(10) Patent No.: US 7,119,899 B2
(45) Date of Patent: Oct. 10, 2006

(54) PARTICLE SENSOR SYSTEM

(75) Inventors: Rocco D. Pochy, Milpitas, CA (US); Scott H. Salton, Fremont, CA (US); Thomas C. Saunders, Milpitas, CA (US); William L. Shade, Jr., San Mateo, CA (US)

(73) Assignee: Lighthouse Worldwide Solutions, Inc, San Jose, CA (US)

( * ) Notice: Subject to any disclaimer, the term of this patent is extended or adjusted under 35 U.S.C. 154(b) by 0 days.

(21) Appl. No.: 10/710,568

(22) Filed: Jul. 21, 2004

(65) Prior Publication Data

US 2006/0017926 A1    Jan. 26, 2006

Related U.S. Application Data

(60) Provisional application No. 60/489,622, filed on Jul. 23, 2003.

(51) Int. Cl.
*G01N 21/00* (2006.01)

(52) U.S. Cl. ........................... 356/338; 356/342
(58) Field of Classification Search ............... 356/336, 356/337, 338, 339, 340, 342
See application file for complete search history.

(56) References Cited

U.S. PATENT DOCUMENTS

| | | | |
|---|---|---|---|
| 3,494,693 A | 2/1970 | Elmer | 362/302 |
| 3,826,574 A * | 7/1974 | Brown, Jr. | 356/339 |
| 3,946,239 A | 3/1976 | Salzman et al. | 356/39 |
| 4,186,838 A * | 2/1980 | Levitt et al. | 209/581 |
| 4,320,978 A * | 3/1982 | Sato | 356/440 |
| 4,422,761 A * | 12/1983 | Frommer | 356/338 |
| 4,942,305 A * | 7/1990 | Sommer | 250/574 |
| 5,767,967 A * | 6/1998 | Yufa | 356/336 |
| 5,838,429 A * | 11/1998 | Hahn | 356/39 |
| 6,239,710 B1 * | 5/2001 | Oppelt | 340/630 |
| 2003/0058451 A1 * | 3/2003 | Foley et al. | 356/437 |
| 2004/0042008 A1 * | 3/2004 | Wagner et al. | 356/337 |

* cited by examiner

*Primary Examiner*—Gregory J. Toatley, Jr.
*Assistant Examiner*—Roy M. Punnoose
(74) *Attorney, Agent, or Firm*—Michael L. Greenberg, Esq.; Greenberg & Lieberman LLC

(57) ABSTRACT

A device is illustrated for detecting particles in a fluid that can detect smaller particles without the need for added power or space and can be implemented inexpensively. The device utilizes two mirrors and a photo-diode. The housing of the photo-electric diode is machined to form one of the mirrors. The mirrors have a special positioning so that the second mirror uses the first mirror to reflect light deflected by particles back to the photo-electric diode.

19 Claims, 3 Drawing Sheets

PARTICLE SENSOR SYSTEM

CROSS REFERENCE TO RELATED APPLICATIONS

Priority is hereby claimed to Provisional Patent Application No. 60/489,622 filed on Jul. 23, 2003.

BACKGROUND OF INVENTION

A device that uses light to detect particles in a fluid, where two mirrors are used to reflect deflected light back to a light detecting device and one of the mirrors is formed from the housing of the light-detecting device.

Because of the small size of semiconductors when manufacturing semiconductors it is critical that particles not be permitted to contaminate the process. Particles as small as 1 µm and less can contaminate the process. The first generation of semiconductor manufacturing plants were built with the so-called open ballroom concept. Here an attempt to keep the entire plant free of particles was made. Each successive generation of manufacturing plant design has made the clean space where particles are eliminated smaller and smaller. The latest design of manufacturing plants has what are called mini-environments. These environments are just big enough to contain the tools that work on the silicon wafers. Silicon wafers are transported from tool to tool in containers that attach to the tools in a process that is analogous to two space ships docking. The goal is to eliminate the possibility of particles entering into either the wafer's transport pod or the tool's mini-environment.

There is a need to constantly monitor the tool's mini-environment to prevent expensive silicon wafers from being contaminated by particles. The tool's mini-environment is essentially no larger then necessary to contain the tool. Because adding space to these mini-environments is expensive and semiconductors are continuously getting smaller and smaller, there is a need for particle detectors to remain small yet detect smaller and smaller particles.

A basic design for a particle detector is illustrated in FIG. 1. The components are shown suspended in space to facilitate understanding their relationship with one another. The three basic components are a light source (10), a light detection device (20), and a source of particle flow (30). Three axes (1,2,3) are illustrated that are normal to each of the three basic components. These axes can be normal to one another as in Euclidian geometry, but they need not be. Arrow (31) indicates the direction of particle flow. Arrow (11) indicates the direction of the light (15). In most relevant art, the light source (10) is a laser, the light detection device (20) is a photodiode, and the particle flow (30) is achieved with a conventional pump (not shown) pushing or pulling the particles along axis 3.

In the FIGS. 1, 3, and 5, the light rays (15) being emitted by the light source (10) are represented as lines as is the custom with ray tracing. And, the particles (35) are represented by small circles. The sizes of the particles (35) are exaggerated for illustrative purposes. The particles (35) come out of the particle source (30) with some velocity and intersect with the light rays (15). The view volume (40) corresponds to the three dimensional intersection of the particle flow (35) and the light rays (15). The view volume (40) is represented by a sphere, as is the custom in discussing particle detectors.

An example of how particles (35) are detected will now be explained. A simple model of light (15) will be used so that ray tracing can be used in order to illustrate the basic method of operation. The particle flow (35) goes through the view volume (40), and light rays (15) strike the particles (35). First light ray 101, third light ray 103, fourth light ray 104, and fifth light ray 105 have collided with particles (35) in FIG. 1 and are scattered. For purposes of discussion, these four light rays (101, 103, 104, 105) will be called scattered light rays (101, 103, 104, 105). Second light ray 102 does not collide with a particle (35). Most light (15) would not collide with a particle (35) and would merely pass through the view volume (40) and proceed down the axis 1. In most relevant art, the light rays (15) will enter a conventional light trap (not shown). Fourth light ray (104) will collide with the light detection device (20); however, the first light ray (101), the third light ray (103), and 105 will not collide with the light detection device (20).

The fourth light ray (104) striking the light detector (20) is used to define the existence of the struck particle (33) and based on the signal strength, the size of the particle (33). The ability to accurately count and size particles is based on the signal strength above the background noise of the system. The greater the signal to noise ratio, the smaller the particle that can be detected and sized. The noise of the system is caused by stray light striking the light detection device (20).

The more of the light rays (101, 103, 104, 105) that were scattered in the viewing sphere that are collected by striking the light detection device (20) the more sensitive the particle detector will be. Relevant art is concerned with increasing the particle detector's ability to record the scattered light rays (101, 103, 104, 105) by redirecting the scattered light rays (101, 103, 105) that would miss the light detection device (20). This redirection is accomplished with mirrors.

The basic principle is that the more of the scattered light rays (101, 103, 104, 105) that can be detected by the light detection device (20), then the more sensitive the particle detector will be, and the less power the particle detector (20) will need to consume for a given sensitivity by the laser (10).

FIG. 2 is a top view of an improved particle detector. A mirror (50) has been added to the basic design and placed on the opposite side from the light detection device (20). The particle flow (35) is not shown in FIG. 2, but is coming into the paper at a right angle. The light rays (15) travel along axis 1 and collide with particles inside the view volume (40) and are scattered. The mirror (50) reflects tenth light ray (110), eleventh light ray (111), twelfth light ray (112), and thirteenth light ray (113) that would have been missed by the light detection device (20) onto the light detection device (20). This is accomplished by making the mirror (50) an ellipsoidal mirror (50) with one focal point (51) at the view volume (40) and the second focal point (52) at the light detection device (20). This arrangement relies on a basic property of ellipsoidal mirrors (50), where a light ray (15) that originates at one focal point (51) will be reflected by the ellipsoidal mirror to the other focal point (52).

In FIG. 2, sixteenth light ray (116), and seventeenth light ray (117) are scattered by striking particle (35) and go directly to the light detection device (20). Not shown is the light that is scattered and still not collected, because it does not hit either the mirror (50) or the light detection device (20). The mirror (50) improves the signal strength at the light detector (20) by focusing the scattered light rays, the tenth light ray (110), the eleventh light ray (111), the twelfth light ray (112), and the thirteenth light ray (113), from the opposite side of the light detection device (20). U.S. Pat. No. 4,422,761 issued to Frommer on Dec. 17, 1983, illustrates this basic one mirror design, where the viewing volume (40) is at one of the foci (51, 52) of an ellipsoidal mirror (50).

The limitation of the one ellipsoidal mirror (50) design illustrated in FIG. 2 by Frommer is that the fourteenth light ray (114) and the fifteenth light ray (115) are scattered by the particles (35), but are not captured by the detector (20). This reduces the sensitivity of the particle sensor. One possible solution to this problem is to increase the size of the light detection device (20); however, any larger light detection device (20) is very expensive and requires custom manufacturing.

The relevant art deals with methods of reflecting the fourteenth light ray (114) and the fifteenth light ray (115), the missed scattered light rays, with a second mirror opposite the first mirror. U.S. Pat. No. 5,767,967 issued to Yufa on Jun. 16, 1998, illustrates an arrangement of two opposing ellipsoidal mirrors, where as in FIG. 2, the viewing sphere (40) is at the focus of an ellipsoidal mirror. However, the device requires a second ellipsoidal mirror that is both expensive and requires space behind the light detection device (20). Further, the device requires a spherical light detection device (20), which would be very expensive to manufacture.

The added space for the second ellipsoidal mirror makes it difficult to construct a small particle detector. Small particle detectors are needed for making hand-held devices and for fitting particle detectors in larger devices such as silicon wafer tools. Further, the added space needed behind the light detection device (20) by the second ellipsoidal mirror prevents upgrading existing single mirror detectors as there is not enough room in the particle detector's housing to accommodate this extra room.

Thus a need has been established for a particle detector based on an ellipsoidal mirror (50) with a viewing volume (40) at one of its foci that has a second mirror that is not expensive to manufacture and does not require an increase in the volume required to house the particle detector. And further, that does not require a special light detection device (20).

SUMMARY OF INVENTION

A device is illustrated for detecting particles in a fluid that uses a first ellipsoidal mirror with a viewing sphere at one of the foci and a light detection device at the second foci. The viewing sphere is where the fluid flow and the light intersect. The light is supplied by a conventional laser. The device's sensitivity is proportional to the percentage of the light that is scattered by particles in the viewing sphere that then reach the light detection device.

A second mirror is used to increase the amount of scattered light that reaches the light detection device. The light detection device is flush with the second mirror so as to minimize the volume needed to house the particle detector. The second mirror uses the first mirror by reflecting the light back through the first focal point of the first mirror so that the first mirror then reflects the light back to the light detection device.

In the preferred embodiment, the first mirror is ellipsoidal and has a first focal point at the center of the viewing sphere and a second focal point at the light detection device. The second mirror is spherical with a radius or center of curvature at the center of the viewing sphere. This arrangement allows the second mirror to use the first mirror to get the scattered light to the light detection device and allows the mirrors to be as compact as possible.

In the preferred embodiment, the second mirror is made inexpensively by machining the housing of the photoelectric diode into the proper spherical shape with a radius equal to the distance between the surface of the second mirror and the viewing sphere. The use of the housing of the photo-electric diode allows for the minimum additional space and is very inexpensive to implement. It further allows for existing particle detectors to be fitted with the new mirror.

DETAILED DESCRIPTION

Figure 1:
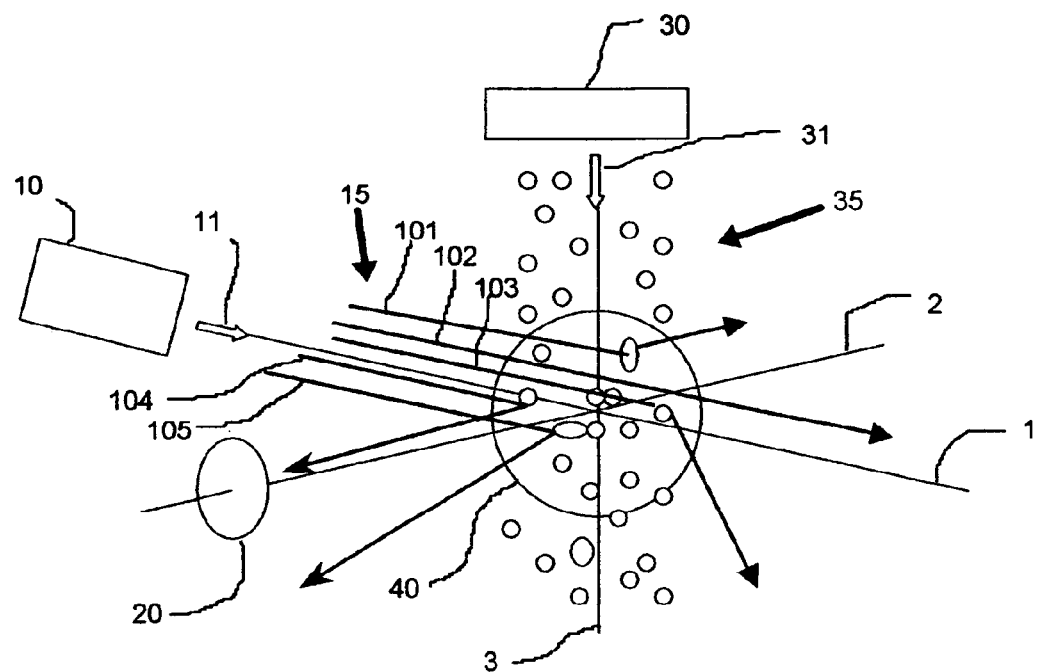
FIG. 1 shows the basic design of a particle detector that uses light.
Figure 2:
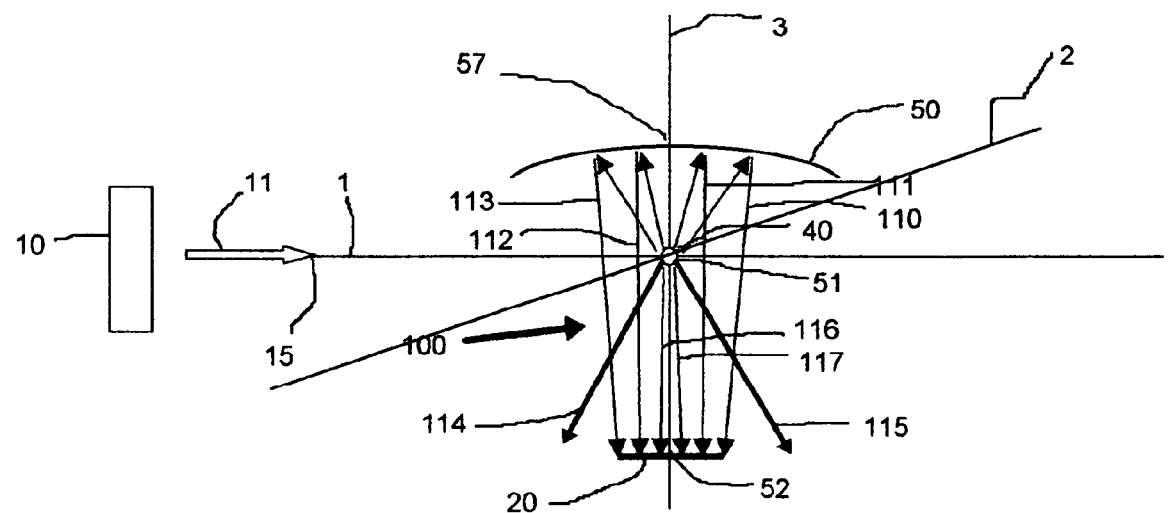
FIG. 2 shows the basic design of a particle detector that uses one ellipsoidal mirror.
Figure 3:
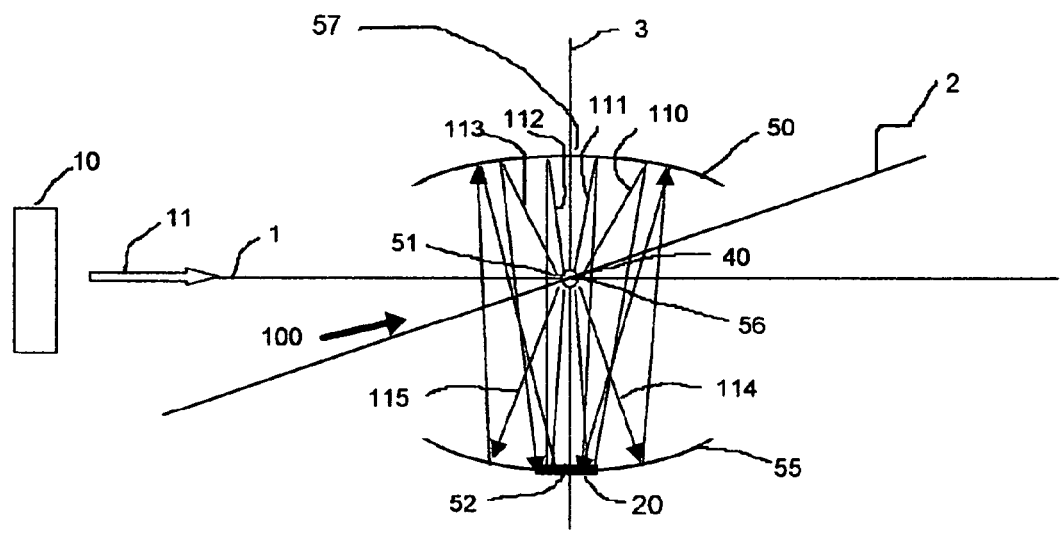
FIG. 3 shows the basic configuration of the present invention.

FIG. 3 illustrates the configuration of the present invention. Here the first mirror (50) is ellipsoidal in shape; however, a concave spherical mirror could also be used as will be discussed later. The particle flow (35) is not shown as it was not in FIG. 2, but is coming into the paper at a right angle. A second mirror (55) is added to the device of FIG. 2. The second mirror (55) captures more of the scattered light (100) on the side of the light detector (20). This is done because the second mirror (55) reflects light back to the first mirror (50), which then reflects the light back to the light detector (20). The fourteenth light ray (114) and the fifteenth light ray (115) illustrate this path. The fourteenth light ray (114) and the fifteenth light ray (115) would have gone past the light detector (20) unrecorded as illustrated in FIG. 2, but instead are reflected back to the first mirror (50), and then reflected onto the light detector (20).

The second mirror (55) is a concave spherical mirror with first focal point (56) at the center of the viewing volume (40) and a second focal point (57) at the center of the first mirror (50). The nomenclature of object location for the first focal point (56) and image location for the second focal point (57) is often used. This arrangement is possible as long as the first focal point (56) is between the radius of curvature of the second mirror (55) and the focal point of the second mirror (55). This is a well-known physical property of a concave spherical mirror. The first and second focal points (51, 52) of the first mirror (50) do not change with the first focal point (51) at the center of the viewing volume (40) and the second focal point (52) at the light detection device (20). This is possible as the light detector (20) sits essentially flush with the second mirror (55). The light detection device (20) can be slightly raised or slightly recessed without changing the fundamental properties of the system.

The addition of the second mirror (55) can almost double the light gathering power of the device. Of great concern to the design of the present invention is not increasing the size of current particle detectors and implementing the second mirror (55) at a very low cost. A further goal is to allow existing particle sensors to be upgraded, so that they can detect smaller particles. The second mirror (55) allows for the current design of particle detectors to detect smaller particles without modifying the other components such as the power supply.

Figure 4:
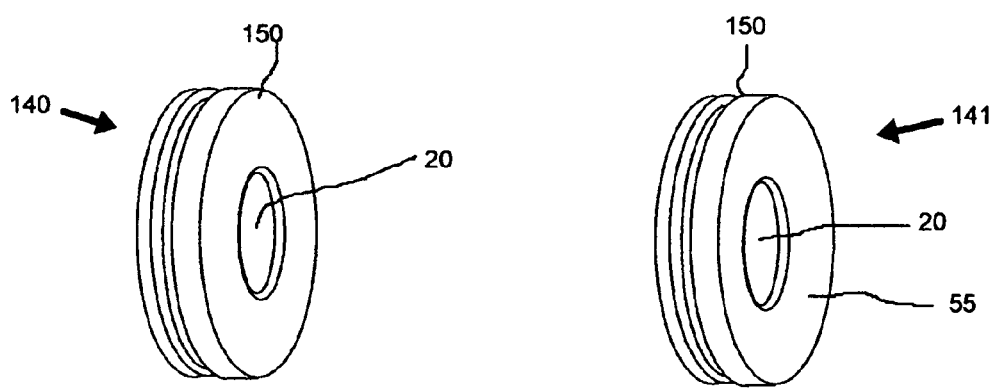
FIG. 4 shows a photo-electric diode with its housing and a photo-electric diode of the present invention with its housing machined in the shape of a spherical mirror.

As illustrated in FIG. 4, these goals are accomplished in the preferred embodiment by machining the second mirror (55) from the holder (150) of the light detector (20), which in the preferred embodiment is a photo-electric diode (20). The holder (140) before machining and the holder after machining (141) are illustrated in FIG. 4. After machining, the holder (150) would have a mirror surface applied to its inside surface (55). The photo-diode (20) then sits just under the mirror surface (55). In the preferred embodiment the mirror surface created would be a spherical surface with a radius equaling the distance between the center of the viewing sphere (40) and a point on the photo-diode (20) surface holder (150), so that both foci of the second mirror (55) would be at the center of the viewing sphere (40). This is due to a well physical property of spherical mirrors that a light ray originating at the center of curvature will be reflected back to the center of curvature, where the center of curvature for a spherical mirror is the radius.

In FIG. 4, the photo-electric diode (20) is slightly recessed from the second mirror (55). This arrangement optimally uses the holder (140) of the photo-electric diode as the spherical mirror (55). The placement of the photo-electric diode (20) can be in one of three places: flush with the second mirror (55), above the second mirror (55), or as in the preferred embodiment below the second mirror's (55) reflective surface. If the photo-electric diode is flush with the second mirror (55), then the curvature of the spherical mirror (55) is defined by how far the photo-electric diode (20) is from the first focal point (51) of the first ellipsoidal mirror (55). The relationship of the photo-electric diode (20) to the second mirror (55) can be varied slightly to optimize such factors as full use of the holder (140), volume needed for the device, and minimizing gaps between the first ellipsoidal mirror (50) and the second spherical mirror (55).

Figure 5:
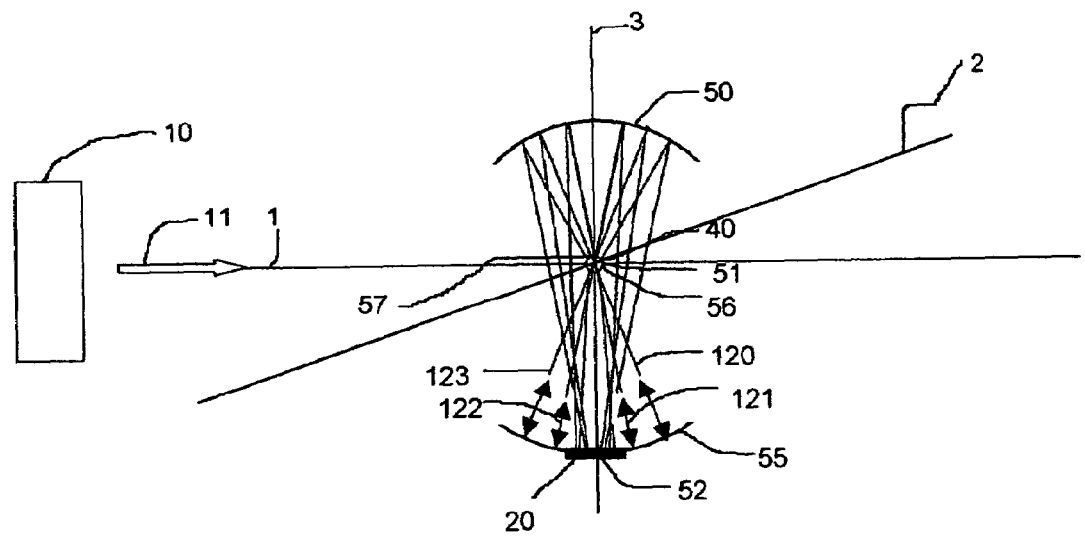
FIG. 5 shows a spherical second mirror of the present invention and light rays.

FIG. 5 illustrates the foci configuration for the preferred embodiment. As in FIGS. 2 and 3, the particle flow (35) is coming into the page to meet with the light flow (15) at the viewing sphere (40). The twentieth light ray (120), the twenty-first light ray (121), the twenty-second light ray (122), and the twenty-third light ray (123) illustrate the special path these light rays take due to the configuration and shape of the mirrors (50, 55). The twentieth light ray (120), the twenty-first light ray (121), the twenty-second light ray (122), and the twenty-third light ray (123) are scattered off particles (35) in the viewing sphere (40) and reflect directly back through the viewing sphere (40) and then to the first mirror (50), and finally back to the light detection device (20). This light path is accomplished by having the two foci of the second mirror (55) that is a concave spherical mirror both be at the viewing sphere (40) and having the first focus (51) of the first mirror (50) be at the view sphere (40) and the second focus (52) of the first mirror (50) be at the surface of the light detection device (20), which in the preferred embodiment is a photo-electric diode (20).

Figure 6:
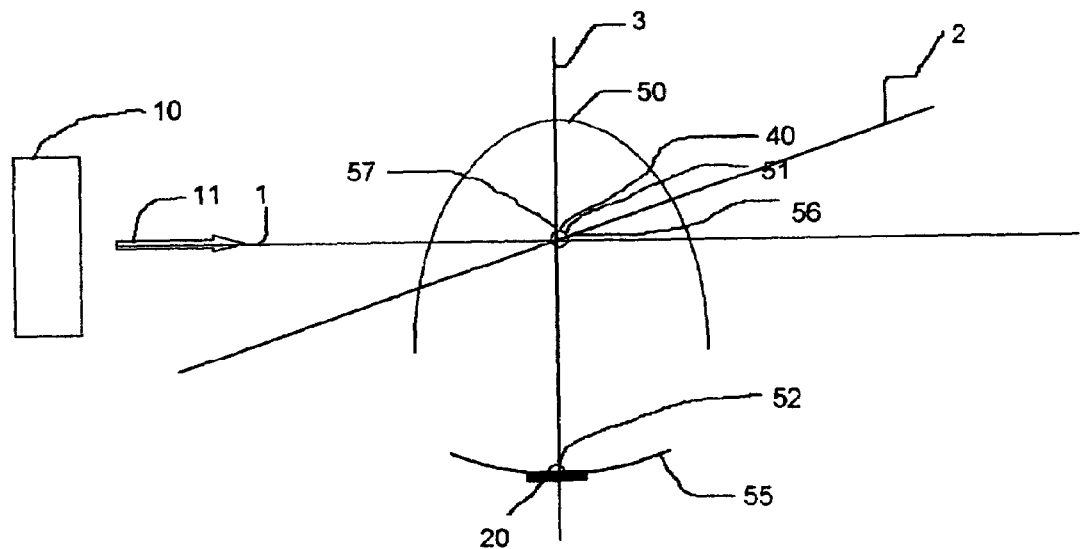
FIG. 6 shows a spherical second mirror of the present invention without light rays.

FIG. 6 is another illustration of the preferred embodiment without the light rays (15) so that the focal points and the shapes of the mirrors (50,55) can be more easily seen. The first mirror (50) is larger then in previous Figures and clearly shows how the first focal point (51) is contained within its three-dimensional shape. The particle flow (35) and the light flow (15) both must pass through the walls of the first mirror (50) and thus require holes in the sides of the first mirror (50). The first mirror's (50) second focal point is at 52. Thus, the first mirror (50) will reflect light originating at the viewing sphere (40) to the photo-electric diode (20).

The second mirror (55) is seen with the photo-electric diode (20) in its center. The second mirror is spherical with a radius from the photo-electric diode (20) to the first focal point (51) of the first mirror (50). This curvature means that the light (15) that is reflected from the second mirror (55) will reflect right back through the viewing sphere (40) or the first focal point (51) of the first mirror (50).

The second mirror (55), then in effect is taking advantage of the first mirror (50) to reflect the rays back to the photo-electric diode (20). This arrangement allows for minimum space to be used to collect the light rays (15) that are not reflected by the first mirror (50).

The preferred embodiment can detect smaller particles without the need for added power or space and can be implemented inexpensively. Furthermore, it can be used to economically upgrade existing particle sensors.

In the preferred embodiment the first mirror (50) is an ellipsoidal shaped mirror. The ellipsoidal shape is preferred as it has a perfect focus from the very center of the first focal point (51), where the viewing volume (40) is located, to the second focus point (52) where the light detection device (20) is located. Spherical mirrors, on the other hand, have inherent aberrations and cannot precisely focus light rays as ellipsoidal mirrors can. This is a well-known physical property of spherical mirrors. However, the advantage to the ellipsoidal shape is only at the very center of the first focal point (51).

A concave spherical mirror can replace the first mirror (50). In this configuration, the viewing sphere (40) is located between the first mirror's (50) focal length and the first mirror's (50) center of curvature. This means that the imagine location formed by this arrangement will be outside the first mirror's (50) center of curvature. A concave mirror is a slice of a sphere, and the line passing through the center of the sphere and attaching to the spherical mirror in the exact center of the mirror is known as the principal axis. The principal axes of the two spherical mirrors would be aligned in the arrangement described above.

In the preferred embodiment that uses an ellipsoidal mirror for the first mirror (50), an axis is defined by the two foci (51, 52) of the first mirror (50). The axis that is defined by the two foci (51, 52) of the first mirror (50) is co-axial with the principal axis of the second mirror (55).

Having illustrated the present invention, it should be understood that various adjustments and versions might be implemented without venturing away from the essence of the present invention. The present invention is not limited to the embodiments described above, and should be interpreted as any and all embodiments within the scope of the following claims.

The invention claimed is:
1. A particle sensor comprising:
a light detection device;
a housing in communication with said light detection device;
a first concave reflective surface on said housing;
wherein said reflective surface has a first focal point and a second focal point defining a first axis of symmetry;
a second reflective surface having a concave ellipsoidal shape;
wherein said second reflective surface has a first focal point and a second focal point defining a second axis of symmetry; and
a means for conducting a gas stream with small particles through the said first focal point of said second reflective surface; and
a means for projecting light through the said first focal point of said second reflective surface.

2. The device of claim 1 wherein said light detection device is circumscribed by said housing.

3. The device of claim 1 wherein said light detection device is a photodiode.

4. The device of claim 1 wherein said reflective surface is gold.

5. The device of claim 1 wherein said light detection device is recessed below said concave reflective surface.

6. The device of claim 1 wherein said light detection device is raised above said first concave reflective surface.

7. The device of claim 1 wherein said light detection device forms the center of said concave reflective surface.

8. The device of claim 1 wherein said reflective surface has a first focal point and a second focal point defining a first axis of symmetry.

9. The device of claim 8 wherein said light detection device is located in the center of said first axis of symmetry.

10. The device of claim 8 further comprising:
a second reflective surface having a concave ellipsoidal shape;
wherein said second reflective surface has a first focal point and a second focal point defining a second axis of symmetry;
wherein said first symmetry of axis and said second axis of symmetry are coaxial.

11. The device of claim 10 further comprising:
a means for conducting a gas stream with small particles through the said first focal point of said second reflective surface; and,
a means for projecting light through the said first focal point of said second reflective surface.

12. The device of claim 1 further comprising:
a second concave spherical reflective surface with a second axis;
wherein said first concave reflective surface is spherical with first principal axis;
wherein said first principal axis and said second axis are co-axial;
a means for conducting a gas stream with small particles through the said second axis of said second reflective surface;
a means for projecting light through the said second axis of said second reflective surface intersecting said gas stream with small particles defining a first intersection point;
wherein the said second concave reflective surface's image location of said first intersection point is at the center of said light detection device; and,
wherein the said first concave reflective surface's radius of curvature is equal to the distance between said first intersection point and said first concave reflective surface where it intersects with said first principal axis.

13. The device of claim 1 further comprising:
a second reflective surface having a concave shape configured to reflect light opposite said first concave reflective surface.

14. A particle sensor comprising:
a first reflective surface having a concave shape;
wherein said first reflective surface has a first focal point and a second focal point defining a first axis of symmetry;
a second reflective surface having a concave ellipsoidal shape;
wherein said second reflective surface has a first focal point and a second focal point defining a second axis of symmetry; and,
wherein said first symmetry of axis and said second axis of symmetry are coaxial;
a means for conducting gas stream with small particles through the said first focal point of said second reflective surface;
a means for projecting light through the said first focal point of said second reflective surface;
a housing in communication with said first reflective surface; and
a means for detecting light in communication with said housing.

15. The device of claim 14 wherein said second focal point of said second reflective surface is located on said first reflective surface at said first axis of symmetry.

16. The device of claim 14 wherein said first focal point of said first reflective surface is coincident with said first focal point of said second reflective surface.

17. The device of claim 14 wherein said second focal point of said first reflective surface is coincident with said second reflecting surface at said first axis of symmetry.

18. The device of claim 14 wherein said means for detecting light is located on said first reflective surface coincident with said first axis of symmetry.

19. The device of claim 14 further comprising:
a light detection device in communication with said first reflective surface;
wherein said first reflective surface is spherical;
wherein said light detection device is centered on said first axis of symmetry;
wherein the radius of curvature for said first reflective surface is equal to the distance between said light detection device at said first axis of symmetry and said first focal point of said second reflective surface.

* * * * *